(12) United States Patent
Kayyali et al.

(10) Patent No.: US 11,872,029 B1
(45) Date of Patent: Jan. 16, 2024

(54) DEVICES AND METHODS FOR SLEEP DISORDER DIAGNOSIS AND TREATMENT

(71) Applicant: Cleveland Medical Devices Inc., Cleveland, OH (US)

(72) Inventors: Hani Kayyali, Shaker Heights, OH (US); Robert Schmidt, Ft. Myers, FL (US); Mohammad Modarres-Zadeh, Tampa, FL (US); Brian Kolkowski, Leroy, OH (US)

(73) Assignee: Cleveland Medical Devices Inc., Cleveland, OH (US)

( * ) Notice: Subject to any disclaimer, the term of this patent is extended or adjusted under 35 U.S.C. 154(b) by 0 days.

(21) Appl. No.: 18/105,277

(22) Filed: Feb. 3, 2023

Related U.S. Application Data

(63) Continuation of application No. 17/825,266, filed on May 26, 2022, now Pat. No. 11,602,284, which is a
(Continued)

(51) Int. Cl.
*A61B 5/085* (2006.01)
*A61B 5/08* (2006.01)
(Continued)

(52) U.S. Cl.
CPC ............ *A61B 5/085* (2013.01); *A61B 5/4815* (2013.01); *A61B 5/02055* (2013.01); *A61M 16/0051* (2013.01); *A61M 16/0069* (2014.02); *A61M 2016/0027* (2013.01); *A61M 2016/0039* (2013.01); *A61M 2202/0208* (2013.01);
(Continued)

(58) Field of Classification Search
CPC ... A61B 5/085; A61B 5/4815; A61B 5/02055; A61M 16/0051; A61M 16/0069; A61M 2016/0027; A61M 2016/0039; A61M 2202/0208; A61M 2205/3553; A61M 2205/3561; A61M 2205/3584; A61M 2205/3592; A61M 2230/04; A61M 2230/10; A61M 2230/14; A61M 2230/202; A61M 2230/205; A61M 2230/60
See application file for complete search history.

(56) References Cited

U.S. PATENT DOCUMENTS

| | | |
|---|---|---|
| 5,704,345 A | 1/1998 | Berthon-Jones |
| 6,167,258 A | 12/2000 | Schmidt et al. |

(Continued)

FOREIGN PATENT DOCUMENTS

| | | |
|---|---|---|
| WO | 2002078775 A2 | 10/2002 |
| WO | 2005028029 A2 | 3/2005 |
| WO | 2005096737 A2 | 10/2005 |

OTHER PUBLICATIONS

Jasemian et al., Evaluation of realtime, remote monitoring telemedicine system using the Bluetooth protocol and a mobile phone network, Journal of Telemedicine and Telecare 2005, vol. 11, Issue 5, at 256.

(Continued)

*Primary Examiner* — Navin Natnithithadha
(74) *Attorney, Agent, or Firm* — Brian Kolkowski

(57) ABSTRACT

The present invention relates to an integrated sleep diagnosis and treatment device, and more particularly to an integrated apnea diagnosis and treatment device. The present invention additionally relates to method of sleep diagnosis and treatment.

20 Claims, 6 Drawing Sheets

Related U.S. Application Data continuation of application No. 16/057,963, filed on Aug. 8, 2018, now Pat. No. 11,375,921, which is a continuation of application No. 13/440,116, filed on Apr. 5, 2012, now Pat. No. 10,076,269, which is a continuation of application No. 11/266,899, filed on Nov. 4, 2005, now Pat. No. 8,172,766.

(51) Int. Cl.
    *A61B 5/0205*     (2006.01)
    *A61M 16/00*     (2006.01)
    *A61B 5/00*     (2006.01)

(52) U.S. Cl.
    CPC ............ *A61M 2205/3553* (2013.01); *A61M 2205/3561* (2013.01); *A61M 2205/3584* (2013.01); *A61M 2205/3592* (2013.01); *A61M 2230/04* (2013.01); *A61M 2230/10* (2013.01); *A61M 2230/14* (2013.01); *A61M 2230/202* (2013.01); *A61M 2230/205* (2013.01); *A61M 2230/60* (2013.01)

(56) References Cited

U.S. PATENT DOCUMENTS

| | | |
|---|---|---|
| 6,287,264 B1 | 9/2001 | Hoffman |
| 6,644,311 B1 | 11/2003 | Truitt et al. |
| 8,069,852 B2 | 12/2011 | Burton et al. |
| 8,187,209 B1 | 5/2012 | Giuffrida |
| 2001/0018557 A1 | 8/2001 | Lynn et al. |
| 2002/0022973 A1 | 2/2002 | Sun et al. |
| 2002/0165462 A1 | 11/2002 | Westbrook et al. |
| 2003/0213489 A1 | 11/2003 | Mechlenberg et al. |
| 2003/0236450 A1 | 12/2003 | Kocinski |
| 2004/0073098 A1* | 4/2004 | Geva ............ A61B 5/7267 600/300 |
| 2004/0129838 A1 | 7/2004 | Lisy et al. |
| 2005/0211249 A1 | 9/2005 | Wagner et al. |
| 2005/0239838 A1 | 10/2005 | Edgar et al. |
| 2007/0161913 A1* | 7/2007 | Farrell ............ A61M 16/06 600/323 |
| 2008/0257349 A1* | 10/2008 | Hedner ............ G16H 20/40 128/204.23 |

OTHER PUBLICATIONS

Woodward et al., Wireless Telemedicine: The Next Step, 4th Int'l IEEE EMBS Special Topic Conference on Information Technology Applications in Biomedicine, 2003, at 43.

Rasid et al., Bluetooth Telemedicine Processor for Multichannel Biomedical Signal Transmission via Mobile Cellular Networks, IEEE Transactions on Information Technology in Biomedicine, vol. 9, No. 1, Mar. 2005, at 35.

Mohd Fadlee A Rasid, Multi-Channel GPRS-Based Mobile Telemedicine System With Bluetooth and J2ME Interfaces, Doctoral Thesis, Department of Electronic and Electrical Engineering, Loughborough University (Oct. 2005).

D. Alan Lankford, Wireless CPAP Patient Monitoring: Accuracy Study, Telemedicine Journal and e-Health, vol. 10, No. 2, 2004, at 162.

R. Paradiso, et al., Wearable Health Care System for Vital Signs Monitoring, 4thAnnual IEEE Conf. on Information Technology Applications in Biomedicine, 2003, at 283.

M. J. Moron, E. Casilari, R. Luque and J. A. Gazquez, A wireless monitoring system for pulse-oximetry sensors, 2005 Systems Communications (ICW'05, ICHSN'05, ICMCS'05, SENET'05), 2005, at 79-84.

Guilleminault C, van den Hoed J, and Mitler MM, Clinical overview of the sleep apnea syndromes. In: C Guilleminault and WC Dement (Eds), Sleep Apnea Syndromes, Alan R Liss, New York, 1978, pp. 1-12.

Christian Guilleminault and Vivien C. Abad, Obstructive sleep apnea syndromes, Med. Clin. N. Am. 88, 2004, pp. 611-630.

Francoise J. Roux and Janet Hilbert, Continuous positive airway pressure: new generations, Clin. Chest Med. 24, 2003, at 315-342.

The AASM Manual for the Scoring of Sleep and Associated Events, 2007.

Kirianaki, et al., Data Acquisition and Signal Processing for Smart Sensors, 2002, John Wiley & Sons Ltd.

Elena, et al., Design of a Mobile Telecardiology System Using GPRS/GSM Technology, Engineering in Medicine and Biology, 2002, Departamento Ingeniería Electrónica, Escuela Superior Ingenieros.

ResMed AutoSet T Service Manual.
ResMed AutoSet Spirit Service Manual 1.
ResMed AutoSet Spirit Service Manual 2.
ResMed AutoSet Spirit Service Manual 3.
ResMed AutoSet Spirit, AutoSet Respond, S7 Elite Service Manual.
Resmed S7 Elite Clinician's Manual.
ResMed AutoSet Spirit, AutoSet Respond, AutoSet S7 Elite Service Manual.
ResMed AutoSet Spirit, AutoSet Respond, AutoSet S7 Elite Service Manual 2.
ResMed S8 AutoSet Vantage System Clinician's Manual.
ResMed S8 Elite/AutoSet Service Manual.
ResMed ResLink Service Manual.
ResMed ResTraxx Quick Reference Guide.
ResMed AutoSet Respond Clinician's Manual.
ResMed ResTraxx Wireless Patient Monitoring Flyer.
ResMed ResTraxx Wireless Patient Monitoring Atlas.
ResMed FDA 510(k) application letter.
ResMed FDA 510(k) application summary.
ResMed VPAP III & VPAP II Series Data Management Guide.
ResMed VPAP II Clinician's Guide.
ResMed AutoScan 5.7 Clinician's Manual, v. 1, 2005.
ResMed AutoScan 5.7 Clinician's Manual, v. 2, 2005.
ResMed AutoScan 5.7 Clinician's Manual, v. 3, 2005.

* cited by examiner

DEVICES AND METHODS FOR SLEEP DISORDER DIAGNOSIS AND TREATMENT

CROSS-REFERENCE TO RELATED APPLICATIONS

This application is a continuation of U.S. patent application Ser. No. 17/825,266, which was filed on May 26, 2022, issued as U.S. Pat. No. 11,602,284 on Mar. 14, 2023, and which is a continuation of U.S. patent application Ser. No. 16/057,963, which was filed on Aug. 8, 2018, issued as U.S. Pat. No. 11,375,921 on Jul. 5, 2022, and which is a continuation of U.S. patent application Ser. No. 13/440,116, which was filed on Apr. 5, 2012, issued as U.S. Pat. No. 10,076,269 on Sep. 18, 2018, and which is a continuation of U.S. patent application Ser. No. 11/266,899, which was filed on Nov. 4, 2005, and issued as U.S. Pat. No. 8,172,766 on May 8, 2012. The specifications and drawings of each of the above patents and applications are hereby incorporated by reference in their entirety.

The U.S. Government has a paid-up license in this invention and the right in limited circumstances to require the patent owner to license others on reasonable terms provided for by the terms of grant number 2R44NS42451 awarded by the National Institutes of Health.

BACKGROUND OF THE INVENTION

1. Field of the Invention

The present invention relates to an integrated sleep diagnosis and treatment device, and more particularly to an integrated apnea diagnosis and treatment device. The present invention additionally relates to method of sleep diagnosis and treatment.

2. Technical Background

Nearly one in seven people in the United States suffer from some type of chronic sleep disorder, and only fifty percent (50%) of people are estimated to get the recommended seven (7) to eight (8) hours of sleep each night. It is further estimated that sleep deprivation and its associated medical and social costs (loss of productivity, industrial accidents, etc) exceed $150 billion dollars per year. Excessive sleepiness can deteriorate the quality of life and is a major cause of morbidity and mortality due to its role in industrial and transportation accidents. Sleepiness further has undesirable effects on motor vehicle driving, employment, higher earning and job promotion opportunities, education, recreation, and personal life.

Sleeping disorders such as for example narcolepsy and sleep apnea are currently diagnosed by two general methods. The first is via subjective methods such as the Epworth and Standford Sleepiness Scale, which generally involves questionnaires where the patients answer a series of qualitative questions regarding their sleepiness during the day. With these methods, however, it is found that the patients usually underestimate their level of sleepiness or they deliberately falsify their responses because of their concern regarding punitive action, or as an effort to obtain restricted stimulant medication.

The second is via physiological based evaluations such as all night polysomnography to evaluate the patients sleep architecture (e.g., obtaining respiratory disturbance index to diagnose sleep apnea) followed by an all day test such as the Multiple Sleep Latency Test (MSLT) or its modified version, Maintenance of Wakefulness Test (MWT). While the MSLT and MWT are more objective and therefore don't have the same limitations as mentioned for the subjective tests, the MSLT and MWT have their own limitations. Both the MSLT and MWT require an all-day stay at a specialized sleep clinic and involve monitoring a number of nap opportunities at two hour intervals throughout the day. Further, the MSLT mean sleep latency is only meaningful if it is extremely short in duration (e.g., to diagnose narcolepsy), and only if the overnight polysomnogram does not show any sleep disordered breathing. Another problem with the MSLT mean sleep latency is the so-called "floor effect" where the sleep latency in the pathologically sleepy patients can be almost zero (0) minutes, i.e., the patient falls asleep almost immediately following turning off the light in the MSLT test. This type of result has a tendency to limit the diagnostic resolution of the test. Finally, studies have shown that the MSLT is not particularly suited for gauging the effects of therapeutic intervention. This was demonstrated in studies by Thorpy in 1992 and Van den Hoed et al. in 1981 showing no reliable reduction in sleepiness in patients given stimulant medications for narcolepsy.

With sleeping disorders such as sleep apnea medications or some physical form of therapy can be used to treat the disorder. The treatment is determined based on one of the above tests, and can be adjusted by re-testing of the patient at some later time to determine whether the condition or the symptoms have been alleviated.

For example, the most common method of treating the sleeping disorder of sleep apnea is by apply a continuous positive gas pressure to the patient's airway, which has the effect of forcing the patient to breath through application of the pressure. More advanced, but still very basic devices have been developed that adjust this continuous positive gas pressure through sensors built into the device for creating the positive gas pressure, which measure gas flow through the device. These basic adjustable devices have been found to be expensive and largely ineffective.

None of the devices on the market can be used to adjust a patient's treatment, whether physical or chemical, based on the patient's current physiological state. Further none of the current devices can be used to adjust a patient's treatment, based on the patient's current symptoms. Still further, none of the current devices can be used to predict the onset of symptoms of various sleeping disorders and provide treatment in anticipation of such symptoms. Still even further, none of the current devices can be used to adjust a treatment device based on the subject's physiological signals.

It is therefore an object of the present invention to provide a system and method of treatment, which analyzes a subject's sleeping disorder or symptoms and adjusts a treatment device based, in part, on this analysis. It is still another object of the present invention to have a closed loop system or partly closed loop system or method, which automatically adjusts a treatment device based on analysis of a subject's sleeping disorder or symptoms. It is still another object of the present invention to provide a system or method for treating a subject's sleeping disorder or symptoms that is predictive. It is still further another object of the present invention to provide a system or method of treating a subject's sleeping disorder or symptoms that uses a subject's physiological signals, e.g., EEG, EKG, EMG, etc.

SUMMARY OF THE INVENTION

The present invention relates to an integrated sleep diagnosis and treatment device, and more particularly to an integrated apnea diagnosis and treatment device. The present invention additionally relates to method of sleep diagnosis and treatment.

There are numerous embodiments of the present invention with a few of those listed below. The present invention further relates to a sleep diagnosis device integrated with a treatment device. The sleep disorder treatment system of the present invention can use a diagnosis device to perform various forms of analysis to determine or diagnose a subject's sleeping disorder or symptoms of a subject's sleep disorder, and using this analysis or diagnosis can with or in some embodiments without human intervention treat the subject either physically or chemically to improve the sleeping disorder or the symptoms of the sleeping disorder. The diagnostic part of the system can use many different types of sensors and methods for diagnosing the severity of the symptoms of or the sleep disorder itself. The treatment part of the system can use a device to physically or chemical treat the subject's symptoms or sleep disorder itself.

The diagnostic part of the system or device can use various sensors for measuring the subject's brain wave signals, respirations and the like. Sensors for measuring the subject's brain wave signals include EEG electrodes and the like. Sensors for measuring the subject's respirations or oxygen levels include sensors to measure airflow, respiratory effort, oxygenation and ventilation, and the like. Measurement of airflow is preferably measured using sensors or devices such as a pneumotachometer, strain gauges, thermal sensors, transducers, piezo sensors, magnetometers, pressure sensors, static charge-sensitive beds, and the like. These sensors or devices, also preferably measure nasal pressure, respiratory inductance plethysmography, thoracic impedance, expired carbon dioxide, tracheal sound and the like. Measurement of respiratory effort is preferably measured by esophageal pressure, surface diaphragmatic EMG, and the like. Measurement of oxygenation and ventilation is preferably measured by pulse oximetry, transcutaneous oxygen monitoring, transcutaneous carbon dioxide monitoring, expired end carbon dioxide monitoring, and the like.

Signals from these sensors are then analyzed to determine the level of severity of the symptoms of the subject's sleep disorder and in some cases to diagnose the sleep disorder itself. One particular embodiment of the present invention involves diagnosing the level of severity of a subject's sleep apnea and with or without human intervention adjusting an apparatus for providing positive airway pressure to the subject. The treatment device can be adjusted by either by a closed loop control system which uses, in part, the data or signals from the diagnosis device to actuate a physical or chemical treatment system for the subject, or an open loop control system which can alert a human who then adjusts the treatment device based in part on the data or signals from the diagnosis device. Alternatively, signals from the sensors can be saved on a medium in order to be retrieved and analyzed at a later date. Media on which data can be saved include, but are not limited to chart recorders, hard drive, floppy disks, computer networks, optical storage, solid-state memory, magnetic tape, punch cards, etc.

The treatment device can be any device known to those skilled in the art. The treatment device can either physically or chemically treat the subject's sleeping disorder. An example of physically treating the subject's sleeping disorder would be a device to provide positive airway pressure to a subject. An example of chemically treating the subject's sleeping disorder would be to have a medication reservoir where a drug is delivered to the subject in order to treat symptoms of the sleeping disorder. A few of the many embodiments of the present invention are as follows.

In one embodiment, the present invention includes a sleeping disorder treatment system comprising a device for diagnosing and creating an output of a level of severity of a subject's sleeping disorder; and a device for physically or chemically treating a subject's sleeping disorder, which can be adjusted using the output of the level of severity of the subject's sleeping disorder.

In another embodiment, the present invention includes a sleep apnea treatment system comprising a device for diagnosing and creating an output of a level of severity of a subject's sleep apnea; and a continuous positive airway pressure (CPAP) device for treating the subject's sleep apnea, whose airflow rate can be automatically adjusted using the output.

In still another embodiment, the present invention includes a sleep apnea treatment system comprising a device for diagnosing sleep apnea comprising EEG sensors, and creating an output of a level of severity of a subject's sleep apnea; and a CPAP device for treating the subject's sleep apnea, which can be automatically adjusted using the output.

In still another embodiment, the present invention includes a sleeping disorder treatment system comprising a device for diagnosing and creating a output of a level of severity of a subject's sleeping disorder or symptoms, comprising at least two EEG electrodes for measuring the subject's electro-physiological signals; and a device for physically or chemically treating a subject's sleeping disorder or symptoms, which can be adjusted using in part the output of the level of severity of the subject's sleeping disorder.

In still another embodiment, the present invention includes a sleeping disorder treatment system comprising a device for diagnosing and creating a output of a level of severity of a subject's sleeping disorder or symptoms comprising at least two ECG electrodes for measuring the subject's brain waves; and a device for physically or chemically treating a subject's sleeping disorder or symptoms, which can be adjusted using in part the output of the level of severity of the subject's sleeping disorder.

In still another embodiment, the present invention includes a sleeping disorder treatment system comprising a device for diagnosing and creating a output of a level of severity of a subject's sleeping disorder or symptoms comprising a sensor for measuring the subject's blood gases; and a device for physically or chemically treating a subject's sleeping disorder or symptoms, which can be adjusted using in part the output of the level of severity of the subject's sleeping disorder.

Finally, in still another embodiment, the present invention includes a sleeping disorder treatment system comprising a device for diagnosing and creating a quantitative output of a level of severity of a subject's sleeping disorder or symptoms comprising a pulse oximeter sensor; and a device for physically or chemically treating a subject's sleeping disorder or symptoms, which can be adjusted using in part the output of the level of severity of the subject's sleeping disorder.

Additional features and advantages of the invention will be set forth in the detailed description which follows, and in part will be readily apparent to those skilled in the art from that description or recognized by practicing the invention as described herein, including the detailed description which follows, the claims, as well as the appended drawings.

It is to be understood that both the foregoing general description and the following detailed description are merely exemplary of the invention, and are intended to provide an overview or framework for understanding the nature and character of the invention as it is claimed. The accompanying drawings are included to provide a further understanding of the invention, and are incorporated in and constitute a part of this specification. The drawings illustrate various embodiments of the invention, and together with the description serve to explain the principles and operation of the invention.

DESCRIPTION OF THE PREFERRED EMBODIMENT

Figure 1:
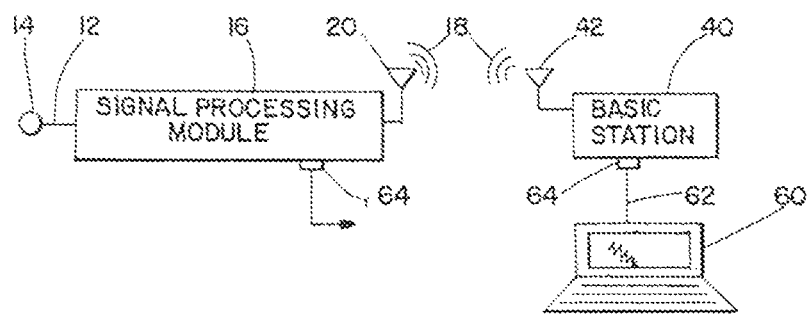
FIG. 1 is a block diagram an embodiment of part of the diagnostic device of sleeping disorder treatment system of the present invention.

The present invention relates to an integrated sleep diagnosis and treatment device, and more particularly to an integrated apnea diagnosis and treatment device. The present invention additionally relates to various methods of an integrating sleep diagnosis and treatment.

The sleep disorder treatment system of the present invention encompasses numerous embodiments. Various embodiments of the present invention include a device for diagnosing and creating an output of a level of severity of the subject's sleeping disorder and/or symptoms. The present invention includes devices and sensors for diagnosing a subject's sleeping disorder and/or symptoms including utilizing a subject's electro-physiological signals such as EEG, EKG, EMG, EOG and the like, a subject's blood gases such as $CO^2$ and $O^2$, and a subject's respiratory patterns using an accelerometer, chest-motion detector and the like.

Sleep apnea is defined as the cessation of breathing during sleep. There are three different types of sleep apnea: obstructive sleep apnea (OSA), central sleep apnea (CSA), and mixed sleep apnea (MSA). Of these three, OSA is the most common; CSA is rare; mixed sleep apnea is a combination of the previous two with treatment being the same as OSA. Treatment of OSA and CSA vary substantially which makes a proper diagnosis of the correct type of sleep apnea (OSA or CSA) critical for an effective treatment.

Obstructive sleep apnea is characterized by repetitive pauses in breathing during sleep due to the obstruction and/or collapse of the upper airway (throat), usually accompanied by a reduction in blood oxygen saturation, and followed by an awakening to breathe. This is called an apnea event. Respiratory effort continues during the episodes of apnoea. Multiple episodes of Apnoea may occur in one night, causing sleep disruption.

Central Sleep Apnea is defined as a neurological condition causing cessation of all respiratory effort during sleep, usually with corresponding decreases in blood oxygen saturation. The brainstem center controlling breathing shuts down there's no respiratory effort and no breathing. This is in contrast with OSA where there is respiratory effort from the brain stem but a physical blockage prevents inhalation of oxygen. The subject is aroused from sleep by an automatic breathing reflex, so the subject may end up getting very little sleep at all. CSA, which is a neuroglial disorder, is very different in cause than OSA, which is a physical blockage-though the effects are highly similar.

Mixed sleep apnoea, as the name suggests, is a combination of the OSA and CSA. An episode of mixed sleep apnoea usually starts with a central component and then becomes obstructive in nature. Generally the central component of the apnoea becomes less troublesome once the obstructive apnoea is treated.

Sensors which can be used are known to those skilled in the art. These sensors include electrodes for measuring electro-physiological signals such as EEG, ECG, EMG, EOG and the like. These electro-physiological signals can be obtained by any method known in the art, or subsequently developed by those skilled in the art to detect these types of signals. Sensors include but are not limited to electrodes or magnetic sensors. Since electro-physiological signals are, in general, electrical currents which produce associated magnetic fields, the present invention further anticipates methods of sensing those magnetic fields to acquire brain wave signals similar to those which can be obtained through, for example, an electrode applied to the subject's scalp. The subject(s) referred to in the present invention can be any form of animal. Preferably the subject(s) are mammal, and most preferably human.

If electrodes are used to pick up the electro-physiological signals, these electrodes for example when measuring brain wave or EEG signals may be placed at one or several locations on the subject(s)' scalp or body. The electrode(s) can be placed at various locations on the subject(s) scalp in order to detect EEG or brain wave signals. Common locations for the electrodes include frontal (F), parietal (P), anterior (A), central (C) and occipital (O). Preferably for the present invention at least one electrode is placed in the occipital position. In order to obtain a good EEG or brain wave signal it is desirable to have low impedances for the electrodes.

Typical EEG electrodes connections may have an impedance in the range of from 5 to 10 K ohms. It is in generally desirable to reduce such impedance levels to below 2 K ohms. Therefore a conductive paste or gel may be applied to the electrode to create a connection with an impedance below 2 K ohms. Alternatively or in conjunction with the conductive gel, the subject(s)' skin may be mechanically abraded, the electrode may be amplified or a dry electrode may be used. Dry physiological recording electrodes of the type described in U.S. patent application Ser. No. 09/949, 055 are herein incorporated by reference. Dry electrodes provide the advantage that there is no gel to dry out, no skin to abrade or clean, and that the electrode can be applied in hairy areas such as the scalp. Additionally if electrodes are used as the sensor(s), preferably at least two electrodes are used—one signal electrode and one reference electrode; and if further EEG or brain wave signal channels are desired, the number of electrodes required will depend on whether separate reference electrodes or a single reference electrode is used. For the various embodiments of the present invention, preferably an electrode is used and the placement of at least one of the electrodes is at or near the occipital lobe of the subject's scalp.

If electrodes are used to pick up the electro-physiological signals, these electrodes for example when measuring cardiac signals using an ECG, may be placed at specific points on the subject's body. The ECG is used to measure the rate and regularity of heartbeats as well as the size and position of the chambers, any damage to the heart and in diagnosing sleeping disorders. As the heart undergoes depolarization and repolarization, electrical currents spread throughout the body because the body acts as a volume conductor. The electrical currents generated by the heart are commonly measured by an array of preferably 12 electrodes, placed on the body surface. Although a full ECG test usually involves twelve electrodes, for the purposes of a sleep study only two are required. These are placed on the subject's left-hand ribcage, under the armpit and on the right-hand shoulder, near the clavicle bone. An ECG is important as a tool to detect the cardiac abnormalities that can be associated with respiratory-related sleeping disorders. Preferably electrodes are placed on each arm and leg, and six electrodes are placed at defined locations on the chest. The specific location of each electrode on a subject's body is well known to those skilled in the art and varies amongst individual and different types of subjects. These electrode leads are connected to a device contained in the signal processing module of the present invention that measures potential differences between selected electrodes to produce electrocardiographic tracings.

There are two basic types of ECG leads: bipolar and unipolar. Bipolar leads (standard limb leads) utilize a single positive and a single negative electrode between which electrical potentials are measured. Unipolar leads (augmented leads and chest leads) have a single positive recording electrode and utilize a combination of the other electrodes to serve as a composite negative electrode.

Other sensors can be used to measure various parameters of a subject's respirations. The subject's respirations can be measured by measurement of airflow, respiratory effort, oxygenation and ventilation, and the like. Measurement of airflow is preferably measuring using sensors or devices such as a pneumotachometer, strain gauges, thermal sensors, transducers, piezo sensors, magnetometers, pressure sensors, static charge-sensitive beds, and the like. These sensors or devices, also preferably measure nasal pressure, respiratory inductance plethysmography, thoracic impedance, expired carbon dioxide, tracheal sound and the like. Measurement of respiratory effort is preferably measured by esophageal pressure, surface diaphragmatic EMG, and the like. Measurement of oxygenation and ventilation is preferably measured by pulse oximetry, transcutaneous oxygen monitoring, transcutaneous carbon dioxide monitoring, expired end carbon dioxide monitoring, and the like.

One example of such a sensor for measuring respirations either directly or indirectly is a respiration belt. Respiration belts can be used to measure a subject's abdominal and/or thoracic expansion over a measurement time period. The respiration belts may contain a strain gauge, a pressure transducer or other sensors, which can indirectly measure a subject's respirations and the variability of respirations by providing a signal which correlates to the thoracic/abdominal expansion/contractions of the subject's abdominal cavity. Respiration belts may be placed at one or several locations on the subject's torso or in any other manner known to those skilled in the art. Preferably, the respiration belts are positioned below the axilla and/or at the level of the umbilicus in order to measure rib cage and abdominal excursions. More preferably, if respiration belts are used then at least two belts are used one being positioned at the axilla and the other at the umbilicus.

Another example of such a sensor or method for measuring respirations either directly or indirectly is a nasal cannula or a facemask. The nasal cannula or facemask can be used to measure the subject's respiratory airflow. Nasal or oral airflow can be measured quantitatively and directly with a pneumotachograph consisting of a standard oxygen nasal cannula or facemask respectively connected to a pressure transducer and placed in the nares or over the subject's mouth and nose respectively. Airflow can be estimated by measuring nasal or oral airway pressure that decreases during inspiration and increases during expiration. Inspiration and expiration produce fluctuations on the pressure transducer's signal that is proportional to airflow. A modified nasal cannula or facemask may also be used which is connected to a carbon dioxide or oxygen sensor to measure respective concentrations of these gases. In addition a variety of other sensors can be connected with either a nasal cannula or facemask to either directly or indirectly measure a subject's respirations.

Still another example of such a sensor or method of either directly or indirectly measuring respirations of the subject is the use of a pulse oximeter. The pulse oximeter can measure the oxygenation of the subject's blood by producing a source of light originating from the oximeter at two wavelengths (650 nm and 805 nm). The light is partly absorbed by haemoglobin, by amounts which differ depending on whether it is saturated or desaturated with oxygen. By calculating the absorption at the two wavelengths the proportion of haemoglobin which is oxygenated can be estimated. Preferably, pulse oximeters are placed on a subject's earlob or fingertip. More preferably, the pulse oximeter is placed on the subject's index finger.

Preferably, the signals from one or more of the aforementioned sensors are fed into some form of device with a processor or relayed to a processor for analyzing the one or more signals from these sensors through either a wireless system, a tethered system or some combination thereof.

One preferable embodiment of this device is a programmable wireless data acquisition system as shown in FIGS. 1-6 and described in more detail herein. This programmable wireless data acquisition system is used to receive the signals from one of more sensors and work with an internal or external processor to analyze the signals. Physiological data is transmitted between the physiological sensors of types described above and the signal processing module using either wired but preferably wireless technology. Once processed, the physiological signals are transmitted wirelessly to the base station. Wireless signals are both received and transmitted via use of a preferably external antenna. Frequencies used for transmission is primarily 902-928 MHz, but frequencies of 2.4-2.484 GHZ, or Wireless Medical Telemetry Bands (WMTS), 608-614 MHz, 1395-1400 MHz, or 1429-1432 MHz can also be used. In addition, IR or Bluetooth wireless technology can be used for data transmission. The communication between the signal processing unit and base station can also, or in addition, be hardwired, instead of wireless. The physiological sensors are generally hard wired to the signal processing unit, but due to the ongoing evolution in wireless sensor technology, signals from physiological sensors will likely be transmitted wirelessly to the signal processing unit, or alternatively, directly to the base station having an integrated signal processing unit.

Referring now to the drawings and, in particular to FIG. 1, there is shown a block diagram of the present invention. An external input 12 from sensor 14 is input to signal processing module 16. Although, one sensor 14 and one external input 12 are shown, the signal processing module 16 is capable of accepting multiple external inputs 12 from multiple sensors 14. The signal processing module 16 generates a signal 18 encoded with data corresponding to the external input 12. The signal processing module 16 transmits the signal 18 by wireless means to a base station 40. In FIG. 1, the wireless means is shown as radio frequency (RF). In this case, the signal processing module generates a radio frequency signal 18 by frequency modulating a frequency carrier and transmits the radio frequency signal through module antenna 20. The base station 40 receives the radio frequency signal 18 through base antenna 42, demodulates the radio frequency signal 18, and decodes the data. It is understood that other wireless means can be utilized with the present invention, such as infrared and optical, for example. Although one module antenna 20 and one base antenna 42 is shown in this embodiment, it is understood that two or more diversity antennas can be used and are included in the present invention. An external programming means 60, shown in FIG. 1 as a personal computer, contains software which is used to program the signal processing module 16 and the base station 40 through data interface cable 62. The data interface cable 62 is connected to the base station 40 and signal processing module 16 by respective connectors 64. The same data interface cable 62 or two different interface cables 62 can be used, one for the base station 40 and one for the signal processing module 16. The signal processing module 16 and the base station 40 can be programmed by connecting a data interface cable 62 between it and an external programming means 60 or by radio frequency (or other type) of signals transmitted between a base station 40 to the signal processing module 16 or to another base station 40. RF signals, therefore, can be both transmitted and received by both signal processing module 16 and base station 40. In this event the signal processing module 16 also includes a module receiver 29 while the base station also includes a base transmitter 84, in effect making both the signal processing module 16 and the base station 40 into transceivers. In addition, the data interface cable 62 also can be used to convey data from the base station 40 to the external programming means 60. If a personal computer is the external programming means 60, it can monitor, analyze and display the data in addition to its programming functions. The base receiver 80 and module receiver 29 can be any appropriate receivers, such as direct or single conversion types. The base receiver 80 preferably is a double conversion superheterodyne receiver while the module receiver 29 preferably is a single conversion receiver. Advantageously, the receiver employed will have automatic frequency control to facilitate accurate and consistent tuning of the radio frequency signal 18 received thereby.

Figure 2:
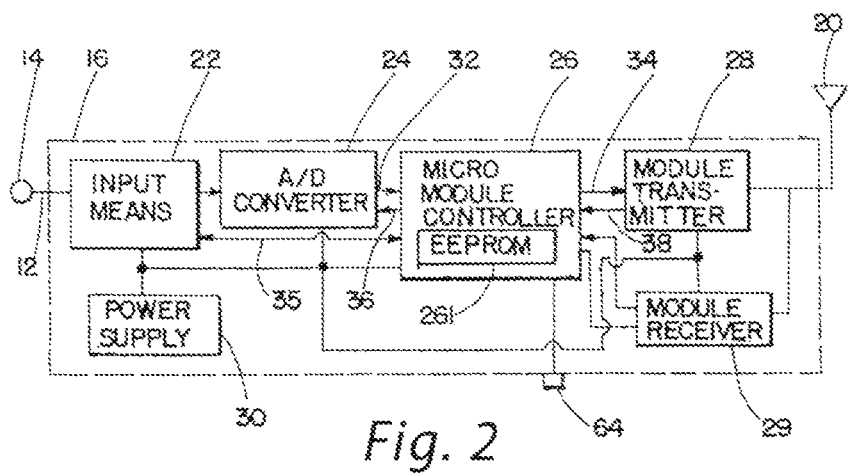
FIG. 2 is a block diagram of an embodiment of the signal processing module of the sleeping disorder treatment system of the present invention.
Figure 3:
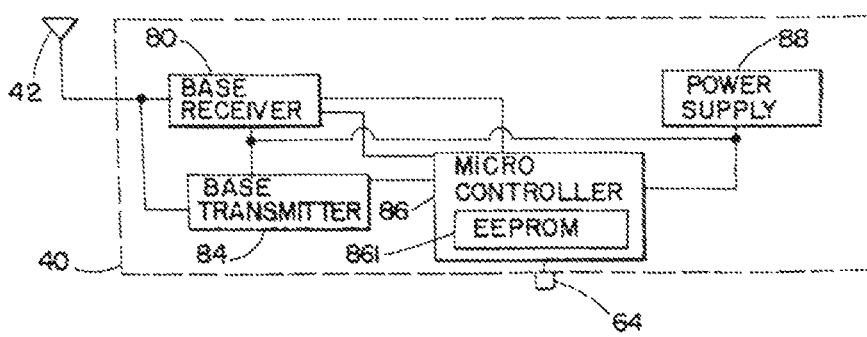
FIG. 3 is a block diagram of an embodiment of a base station of part of the diagnostic device of the sleeping disorder treatment system of the present invention.

Referring now to FIG. 2, there is shown a block diagram of the signal processing module 16 with the sensor 14 and the module antenna 20. The signal processing module 16 comprises input means 22, analog-to-digital (A/D) means 24, a module microcontroller 26 with a nonvolatile memory, advantageously, an EEPROM 261, a module transmitter 28, a module receiver 29 and a module power supply 30. Although the module antenna 20 is shown externally located from the signal processing module 16, it can also be incorporated therein. The module antenna 20 may be a printed spiral antenna printed on a circuit board or on the case of the signal processing module 16 or other type of antenna. A module power supply 30 provides electrical power to the signal processing module 16 which includes the input means 22, A/D means 24, module microcontroller 26 module transmitter 28 and module receiver 29.

The input means 22 is adjustable either under control of the module microcontroller 26 or by means of individually populatable components based upon the specific external input 12 characteristics and range enabling the input means 22 to accept that specific external input 12. For example, if the input is a 4-20 mA analog signal, the input means 22 is programmed by the module microcontroller 26 and/or populated with the components needed to accept that range and characteristic of signals. If the input characteristics change the programming and/or components change accordingly but the same platform circuit board design is utilized. In other words, the same platform design is utilized notwithstanding the character, range, or quantity (number of external inputs 12) [up to a predetermined limit] of the input. For example, bioelectric signals such as EEG, EMG, EKG, and EOG have typical amplitudes of a few microvolts up to a few tens of millivolts. For a given application, a specific frequency band of interest might be from 0.1 Hz to 100 Hz, whereas another application may require measurement of signals from 20 Hz to 10 KHz. Alternatively, measurement of vital signs such as body temperature and respiration rate may deal with signals in a range of +5 volts, with a frequency content from DC (0 Hz) to 20 Hz. For other applications such as industrial process monitoring, the information of interest may be contained in the signal as a current, such as a 4 to 20 mA current loop sensor, or it may take the form of resistance, impedance, capacitance, inductance, conductivity, or some other parameter, The present invention provides a single device for measuring such widely disparate signal types and presents distinct economic advantages, especially to small enterprises such as a medical clinic located in a rural area, which would be empowered by this invention to conduct tests which would otherwise have required patient travel to a large medical center, with all the attendant cost thereof.

This is possible due to the selectively adaptable input means 22 and A/D means 24, the frequency agile module transmitter 28 and base transmitter 84, and the programmability of the module microcontroller 26 and EEPROM 261. One universal platform design then can be utilized for all applications. In addition, the signal processing module can comprise multiple copies of the input means 22 and the A/D means 24. Cost savings can be achieved by multiplexing at several different points in the input means 22 and the A/D means 24 allowing hardware to be shared among external inputs 12.

After receipt by the input means 22, the external input 12 is inputted to the A/D means 24. The A/D means 24 converts the input to a digital signal 32 and conditions it. The A/D means 24 utilizes at least one programmable A/D converter. This programmable A/D converter may be an AD7714 as manufactured by Analog Devices or similar. Depending upon the application, the input means 22 may also include at least one low noise differential preamp. This preamp may be an INA126 as manufactured by Burr-Brown or similar. The module microcontroller 26 can be programmed to control the input means 22 and the A/D means 24 to provide specific number of external inputs 12, sampling rate, filtering and gain. These parameters are initially configured by programming the module microcontroller 26 to control the input means 22 and the A/D means 24 via input communications line 35 and A/D communications line 36 based upon the input characteristics and the particular application. If the application changes, the A/D converter is reconfigured by reprogramming the module microcontroller 26. In this manner, the input means 22 and the A/D means 24 can be configured to accept analog inputs of 4-20 mA, +/−5 volts, +/−15 volts or a range from +/−microvolts to millivolts. They also can be configured to accept digital inputs, for detection of contact closure, for example.

The module microcontroller 26 controls the operation of the signal processing module 16. In the present invention, the module microcontroller 26 includes a a serial EEPROM 261 but any nonvolatile memory (or volatile memory if the signal processing module remains powered) can be used. The EEPROM 261 can also be a separate component external to the module microcontroller 26. Advantageously, the module microcontroller 26 may be PIC16C74A PIC16C74B or a PIC16C77 both manufactured by Micro-Chip, or an Amtel AT90S8515 or similar. The module microcontroller 26 is programmed by the external programming means 60 through the connector 64 or through radio frequency signal from the base station 40. The same module microcontroller 26, therefore, can be utilized for all applications and inputs by programming it for those applications and inputs. If the application or inputs change, the module microcontroller 26 is modified by merely reprogramming. The digital signal 32 is inputted to the module microcontroller 26. The module microcontroller 26 formats the digital signal 32 into a digital data stream 34 encoded with the data from the digital signal 32. The digital data stream 34 is composed of data bytes corresponding to the encoded data and additional data bytes to provide error correction and housekeeping functions. Advantageously, the digital data stream 34 is organized in data packets with the appropriate error correction data bytes coordinated on a per data packet basis. These packets can incorporate data from a single input channel or from several input channels in a single packet, or for some applications may advantageously include several temporally differing measurements of one or a plurality of input channels in a single packet. The digital data stream 34 is used to modulate the carrier frequency generated by the transmitter 28.

The module transmitter 28 is under module microcontroller 26 control. The module transmitter 28 employs frequency synthesis to generate the carrier frequency. In the preferred embodiment, this frequency synthesis is accomplished by a voltage controlled crystal reference oscillator and a voltage controlled oscillator in a phase lock loop circuit. The digital data stream 34 is used to frequency modulate the carrier frequency resulting in the radio frequency signal 18 which is then transmitted through the module antenna 20. The generation of the carrier frequency is controlled by the module microcontroller 26 through programming in the EEPROM 261, making the module transmitter 28 frequency agile over a broad frequency spectrum. In the United States and Canada a preferred operating band for the carrier frequency is 902 to 928 MHz. The EEPROM 261 can be programmed such that the module microcontroller 26 can instruct the module transmitter 28 to generate a carrier frequency in increments between 902 to 928 MHz. as small as about 5 to 10 KHz. In the US and other countries of the world, the carrier frequency may be in the 2400 to 2483.5 MHz. band, 5.725 to 5.875 GHz. band, or the 24.0 to 24.25 GHz. band, or other authorized band. This allows the system to be usable in non-North American applications and provides additional flexibility.

The voltage controlled crystal oscillator (not shown) in the module transmitter 28, not only provides the reference frequency for the module transmitter 28 but, advantageously, also, provides the clock function 38 for the module microcontroller 26 and the A/D means 24 assuring that all components of the signal processing module 16 are synchronized. An alternate design can use a plurality of reference frequency sources where this arrangement can provide certain advantages such as size or power consumption in the implementation.

The module receiver 29 in the signal processing module 16 receives RF signals from the base station 40. The signals from the base station 40 can be used to operate and control the signal processing module 16 by programming and reprogramming the module microprocessor 26 and EEPROM 261 therein.

The base station 40 has a base antenna 42 through which RF signals 18 are received. Base microcontroller 86 controls the operation of the base station 40 including base receiver 80, base transmitter 82, and base power supply 88. Base receiver 80 receives the RF signal 18 from base antenna 42. The base receiver 80 demodulates the RF signal 18 and the base microcontroller 86 removes any error correction and performs other housekeeping tasks. The data is then downloaded through connector 64 to the external programming means 60 or other personal computer (PC) or data storage/viewing device for viewing in real time, storage, or analysis.

Figure 4:
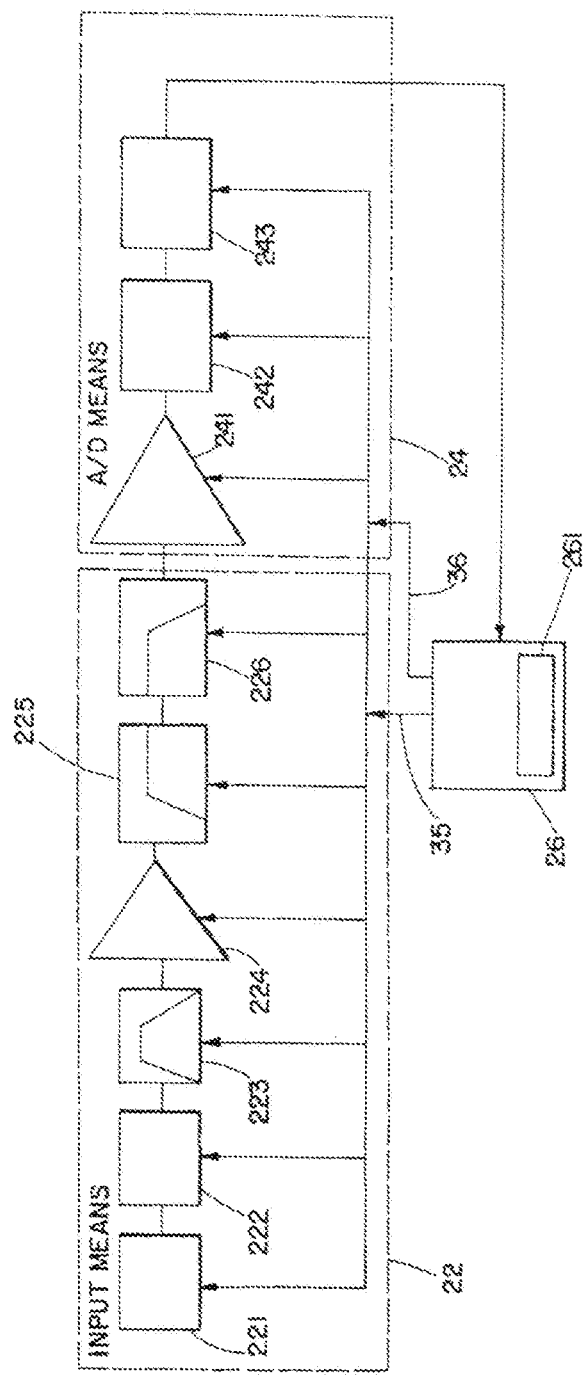
FIG. 4 is a block diagram of an embodiment of a base station of part of the diagnostic device of the sleeping disorder treatment system of the present invention.

Referring now to FIG. 4, there is shown a block diagram of the input means 22 and A/D means 24 of the signal processing module 16, which provides for the data acquisition function of the present invention. The signal processing module 16 is variably configurable through software programming initiated by the external programming means 60 to the EEPROM 261 of the microcontroller 26. The variable configurability enables the signal processing module 16 to receive external inputs 12 having different characteristics and ranges and to provide variable sampling rate, filtering and gain of the external inputs 12 based upon such characteristics and range and/or the specific application. For example, if the present invention is utilized in a biomedical environment, EEG diagnosis and monitoring for instance, the sampling rate will need to be much higher than it would be for an industrial setting measuring thermocouple readings. The ability to reconfigure the system for varying signal characteristics arises at three separate levels in the present invention. For maximum flexibility, such reconfiguration can be carried out during a series of measurements by means of the wireless link, which is understood in this context to be bidirectional. Depending on the characteristics of the received signal 18, the base station 40 can command the signal processing module 16 to reconfigure the input means 22 and/or A/D means 24 to accept an external input 12 of larger amplitude, or a different frequency range, where signal characteristics change significantly during the course of a series of measurements. Alternatively, for cost, size, and power advantages, this adjustment could be carried out prior to a series of measurements, with the configuration information stored in memory in the signal processing module 16, where this memory is advantageously implemented in a nonvolatile form such as EEPROM 261, allowing the configuration information to be retained, for instance, across power outages and obviating the need for module receiver 29 and base transmitter 84, saving cost. A third alternative, which provides advantages in certain technical parameters, is to arrange the implementation of the signal processing module 16 such that minor changes in component values or parameters can reconfigure the same basic hardware to accept widely divergent external input 12 types. This reconfiguration could take place at the factory, providing cost and inventory advantages to the manufacturer, or it could be performed by the end user, providing similar cost advantages to the user in allowing one piece of equipment to perform multiple tasks.

A number of configurable components are shown in FIG. 4. Any given component of this arrangement, though, may be omitted, and, in some cases, the order of the components may be changed to gain certain advantages such as physical size, power consumption, or cost, without changing the basic spirit of the invention. Components in this FIG. 4 may be combined, either by having a single component carry out the function of two or more of the components shown or by combining functions within a single package such as an integrated circuit or hybrid module. Certain components may also operate with a fixed configuration, limiting the flexibility of certain parameters while retaining the advantages of configurability in other components.

The external input 12 inputs to the input protection network 221, which protects the signal processing module 16 against damage caused by faults or unanticipated conditions encountered at the external inputs 12. Depending on the rigors expected to be encountered in any given application and the tolerance to size and weight, the input protection network 221 may be omitted, may consist of a simple resistor network, or may include more elaborate protection such as diodes, zener diodes, transorbs, gas discharge tubes, and other components commonly known to those of ordinary skill in the art. Typically, the input protection network 221 is not configurable but its configurability in the present invention provides advantages in certain applications. Configuration options can include adjustable limits on input voltage and/or current as well as rates of change of those parameters, and other electrical parameters as well. These configuration changes can be achieved by changes to component values on a common platform for smallest size, or can be changed under processor control by means of various switches such as relays. A signal within normally expected ranges passes essentially unchanged to the measurement type means 222.

The measurement type means 222 allows selection of the external input 12 configuration. The measurement type means 222 may be used to configure the input circuitry to accept external inputs 12 which are single-ended voltage (a voltage with respect to a common reference shared between several signals), differential voltage (voltage between two defined conductors), differential current (current flowing through a conductor), single-ended current (current flowing to a common reference), frequency, capacitance, inductance, resistance, impedance, conductivity, or any other electrical parameter. The measurement type means 222 converts the external input 12 to a common parameter such as voltage or current, which can be interpreted by the succeeding blocks regardless of the original type of external signal 12 measured. One input channel can be built with several different measurement type means, which can be selectively enabled by means of an analog switch, such as that found in the AD7714 chip in the present invention. It is understood that the AD7714 chip can provide many of the functions of the A/D means 24 and the input means 22 thus reducing the overall size of the signal processing module 16. In the preferred embodiment, the output of the measurement type means 222 is a varying voltage carrying the information which was present in the original signal, or in certain cases, a series of voltage measurements, which are then conveyed to the prefilter 223.

The prefilter 223 allows rejection of external inputs 12 of large signals which are outside the frequency band of interest, so that such signals do not saturate the low-noise preamplifier 224. The prefilter 223 can be advantageously arranged to be a relatively simple filter to provide cost, size, and power advantages, because it need only reject out of band signals to the extent necessary to protect the low-noise preamplifier 224. A typical application might use a simple "R-C" filter to reject offset voltages in an AC-coupled application, or to reject extremely high frequencies which fall well beyond the frequency band of interest, or a combination of the two. Configurability of this section can be limited to simply enabling or bypassing the prefilter 223, or may be more elaborate in allowing selection of cutoff frequencies. In the preferred embodiment this prefilter consists of a simple RC filter which can be bypassed under firmware control, to minimize noise injection; however, an alternate embodiment could incorporate electrically adjustable components such as electronic potentiometers or varactors to provide even more flexibility at the expense of size and noise injection. The prefiltered signal is then passed to the low-noise preamplifier 224.

The low-noise preamplifier 224 is advantageous in certain applications to allow application of gain to the external input 12 early in the signal chain, before significant noise is introduced by the inherent characteristics of certain components, such as thermal noise. Configurability of the gain applied at this step provides an advantage in allowing the present invention to accept larger external inputs 12 using a low gain (unity gain or lower), or alternatively to accurately measure very small external inputs 12 with minimal noise by using higher gain. This gain can be selectively chosen to be either a fixed value or unity gain under processor control by means of the signal selector built into the AD7714 used in the preferred embodiment, or can be designed to allow a selection of one of several gains by means of analog switches combined with a plurality of gain setting resistors. Gain applied at this stage has the net effect of dividing any downstream noise by the gain factor applied here. This more robust signal output by the preamplifier 224 is then passed to the AC coupling filter 225.

The AC coupling filter 225 is a highpass filter used to allow the system to reject the DC offset or steady state value of an external input 12 wherein the offset is not of interest, allowing additional gain to be applied to the changes in the external input 12. For instance, bioelectric signals such as EEG, EMG, or ECG are normally of interest only for the changes in those signals, and the absolute offset level is not of interest for diagnostic purposes. The cutoff frequency may be configured to allow adjustment of various parameters such as settling time, or may be adjusted to zero to effectively bypass the AC coupling filter 225. In the preferred embodiment, the filter may be bypassed by use of the signal selector switch in the AD7714; however, the use of adjustable components such as electronic potentiometers or varactors would allow more flexibility in choosing the cutoff frequency, at the expense of size and power consumption. The resulting signal, now stripped of any interfering DC offset if so configured, is then passed to the antialias filter 226.

The antialias filter 226 is a lowpass filter required to guard against false signals caused by aliasing between external input 12 content and sampling rate of downstream sampling functions such as multiplexing or analog-to-digital conversion. The Nyquist sampling theorem shows that any frequency content in the sampled signal which is higher than one-half the sampling rate of the sampling function will cause aliasing, which results in false signals. In practice the antialias filter 226 is more commonly set to a smaller fraction of the sampling rate, usually between ¼ and ⅒ the sampling rate. Regardless of the rate or ratio used, the cutoff frequency of the antialias filter 226 must change when the sampling rate changes significantly, to retain the most advantageous ratio of the sampling rate to the filter passband. The programmable cutoff frequency of the antialias filter 226 is thus required to allow for variable sampling rates. In the preferred embodiment, the high sampling rate of the delta sigma modulator in the AD7714 permits the use of a simple fixed RC type filter, with the anitalias filtering begin provided as an inherent digital filter in the AD7714; however, an alternate embodiment might use a switched capacitor filter such as the MAX7409 or other filter with a programmable cutoff frequency. The resulting filtered signal is then conveyed to the programmable gain amplifier 241 in the A/D means 24.

The programmable gain amplifier 241 adjusts the external input 12 amplitude to match the amplitude accepted by the A/D converter 242. In the preferred embodiment this programmable gain amplifier is included in the AD7714 integrated circuit, but this function could also be provided with a dedicated programmable gain amplifier, or alternatively through the use of analog switches or adjustable components such as potentiometers or DACs. If too much gain is applied, the programmable gain amplifier 241 itself or downstream components will saturate, introducing severe distortion and usually rendering the external input 12 unmeasurable. If, on the other hand, insufficient gain is applied here, the quantization noise of the analog-to-digital conversion process comes to dominate the external input 12, causing a severe degradation in the signal-to-noise ratio. For instance, a typical 16-bit A/D converter 242 can distinguish between $2^{16}$ or 65536 distinct levels. With an A/D converter 242 input range of.+−0.3 volts, each level represents 92.$\mu$.V. If insufficient gain is applied to the external input 12 such that the total signal swing is only 200.$\mu$.V, the A/D converter 242 will convert at most three distinct levels, rendering fine features of the external input 12 totally illegible. The module microcontroller 26 therefore adjusts the gain applied in the programmable gain amplifier 241 such that the expected external input 12 as processed and filtered by the preceding elements as described above, is amplified to cover as much of the A/D converter 242 input range as practical, or some other gain which optimizes signal features of interest. Additionally, in some applications it is advantageous to have the module microcontroller 26 adjust this gain dynamically depending upon the actual measured external input 12. For instance, the module microcontroller 26 might increase the programmable gain amplifier 241 gain when a measured external input 12 is very small, and then decrease the gain to avoid saturation when the external input 12 amplitude increases. This automatic gain control provides an increase in the total dynamic range achievable by the system without requiring expensive, large, and power-hungry components such as very high resolution A/D converters 242. The signal resulting from application of the specified gain is then passed to the A/D converter 242.

At least two parameters of a typical A/D converter 242 can be readily adjusted to achieve various goals as the situation dictates. First, the sampling rate may be adjusted to balance the conflicting goals of high fidelity measurements and low digital data rate. Where a signal has no high frequency content of interest, the sampling rate may be adjusted to a very low rate to minimize the demands on downstream processes such as digital filtering or telemetering of the data. On the other hand, sampling an external signal 12 with significant high-frequency content of interest demands a higher sampling rate. In the preferred embodiment, the sampling rate is programmable via the AD7714; in other implementations the sampling rate can be made adjustable by means of an externally applied sampling clock to an A/D converter. The adjustable sampling rate allows the controller to adapt the A/D converter 242 to best meet the system demands of the moment.

In a similar fashion, selection of the resolution provided by the A/D converter 242 must balance faithful reproduction of the external input 12 against total digital data rate. Depending on the particular A/D converter 242 used, there may also be a tradeoff of the maximum achievable sampling rate against the selected resolution, wherein selection of a higher resolution lowers the maximum attainable sampling rate. Again the module microcontroller 26 can adjust this parameter to best meet the system requirements, selecting higher resolution when smaller changes in the measured signal amplitude must be reported, and lower resolution when the lack of such a requirement allows advantages in the form of either a higher sampling rate or a lower digital data rate. In the preferred embodiment, the AD7714 can be programmed to either 16 bit or 24 bit resolution, and the firmware running in the microcontroller can selectively transmit 8, 12, 16, or 24 bits of the acquired data. The digital filter 243, the module microcontroller 26, or other downstream process can also reject certain portions of the digital data stream to provide an effective decrease in resolution where this decrease is advantageous, especially when the data must later cross a bandwidth-limited link such as a RF, IR or optical link. The A/D converter 242 passes the signal, now in the form of a succession of digital values, to the digital filter 243 for further processing.

The digital filter 243 extracts external input 12 parameters of interest while rejecting other signals, commonly referred to as noise. Implementation of the digital filter 243 could alternatively be in the form of analog filters applied anywhere in the signal chain prior to the A/D converter 242, but implementation as a digital filter 243 provides advantages as to programmability, calibration, drift, and accuracy. The digital filter 243 could be implemented in many forms, depending upon the demands of the particular application. In the preferred embodiment, the digital filter is inherent in the analog to digital conversion process inside the AD7714, but it is understood that the digital filter 243 could be implemented as firmware inside the module microcontroller 26 itself, or as a digital signal processor, or as a specialized integrated circuit, or by some other means. Regardless of implementation, the programmability of the digital filter 243 allows the system to readily adapt to changing measurement requirements, whether those changes are brought about by changes in the environment, changes in the external input 12 itself, or changes in the focus of the overall system. The resulting output from the digital filter 243 is a stream of digital values, ready for further processing such as assembly into the desired format for transmission by the firmware.

Figure 5:
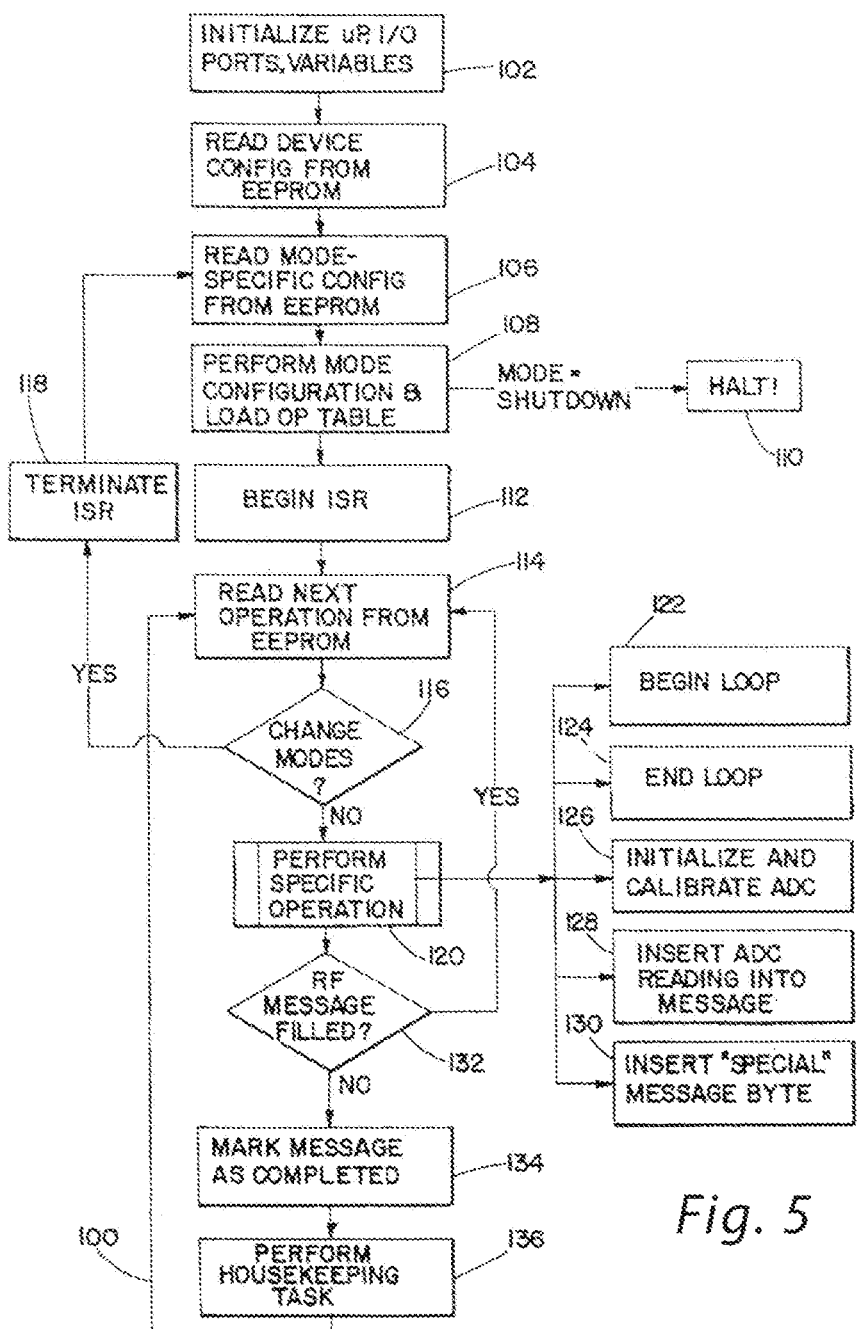
FIG. 5 is a block diagram of an embodiment of the programming firmware in the signal processing module of part of the diagnostic device of the sleeping disorder treatment system of the present invention.

Referring now to FIG. 5 there is shown a block diagram of the firmware of the present invention. The signal processing module 16 firmware defines several modes of operation 100. There are several "test" modes which are used during factory calibration of the device. In addition, there are several operation modes which have mode-specific configuration. For example, the signal processing module 16 can be programmed to operate in a first operational mode in which it transmits calibration data (used to properly zero the analog inputs) for the first three seconds of operation (or for some other predetermined time), and then switches to a second operational mode which transmits analog signal information as collected from the A/D converters 242. The configuration for each mode of operation is programmed in the non-volatile memory EEPROM 261.

Once power is first applied to the signal processing module 16, the module microcontroller 26 performs the basic device initialization, including proper configuration of the I/O ports and internal variables 102. Next, the module microcontroller 26 reads the initial device configuration 104 from the EEPROM 261. This configuration controls the input means 22 of the signal processing module 16, including the number of external inputs (also herein referred to as channels), the resolution of the A/D converter 242, and the sampling rate of each individual input channel. This configuration also controls the operation of the module transmitter 28 in the signal processing module 16, including the carrier frequency, modulation type, output power control, and the length in bytes of each transmitted RF message packet. This configuration also describes the initial mode of operation for the signal processing module 16.

Once the initial configuration has been read, the module microcontroller 26 enters the first mode of operation described in the configuration. It reads the mode-specific configuration 106, which includes the state of the module transmitter 28 and the analog inputs as used in the mode. This configuration can reside in EEPROM 261 or in module microcontroller 26 memory. The module microcontroller 26 then initializes all the peripheral devices according to this mode configuration 108. In the special case that this is the "shutdown" mode, the module microcontroller 26 will perform a software power-down 110.

Once the mode has been initialized, the module microcontroller 26 begins execution of the interrupt service routine (ISR) 112, which is responsible for transmitting the data in the form of messages along the modulated RF carrier. Operation of the interrupt service routine is asynchronous and distinct from the mainline code, and is described later.

The module microcontroller 26 begins execution of the mode-specific "opcodes" 114, which are a sequence of instructions contained either in EEPROM 261 or in the module microcontroller 26 memory. These opcodes are performed for each operational mode. The module microcontroller 26 reads the first operational code from the EEPROM 261 and interprets the opcode, performing an appropriate action: If the opcode instructs the module microcontroller 26 to change modes 116, the module microcontroller 26 terminates the ISR 118 and returns to the mode initialization, and begins execution of a new operational mode; if the opcode instructs the module microcontroller 26 to begin a loop construct 120, the module microcontroller 26 begins the loop by initializing a loop counter variable 122; if the opcode instructs the module microcontroller 26 to end a loop construct, the module microcontroller 26 increments the loop counter variable and determines if the loop is complete 124. If not, the module microcontroller 26 resets the index of current opcode to the beginning of the loop, otherwise it sets the index of the next opcode to after the loop; if the opcode instructs the module microcontroller 26 to initialize a single A/D converter 242, the module microcontroller 26 will perform the specified calibration 126; if the opcode instructs the module microcontroller 26 to the read a single A/D converter 242, the module microcontroller 26 will take the reading and insert the data into the current message to be transmitted over the RF carrier 128; if the opcode instructs the module microcontroller 26 to insert a special byte of data into the RF message, the module microcontroller 26 will insert this data into the message 130. This special message byte may include an identifier to uniquely identify the signal processing module 16, an error check field such as a cyclic redundancy check, or some data representing the internal state of the signal processing module 16 such as the RF frequency, measured temperature, etc.

After each opcode has been read and interpreted, the module microcontroller 26 determines if the RF message has been completely filled and is ready to be transmitted over the RF carrier 132. If it has, the module microcontroller 26 marks a flag variable for the interrupt service routine to begin transmitting the RF message 134.

Next, the module microcontroller 26 performs any housekeeping tasks, such as updating the RF tuning parameters based on changes in temperature, updating timers, etc. 136. Finally, the module microcontroller 26 returns to execute the next opcode in the sequence 114.

Figure 6:
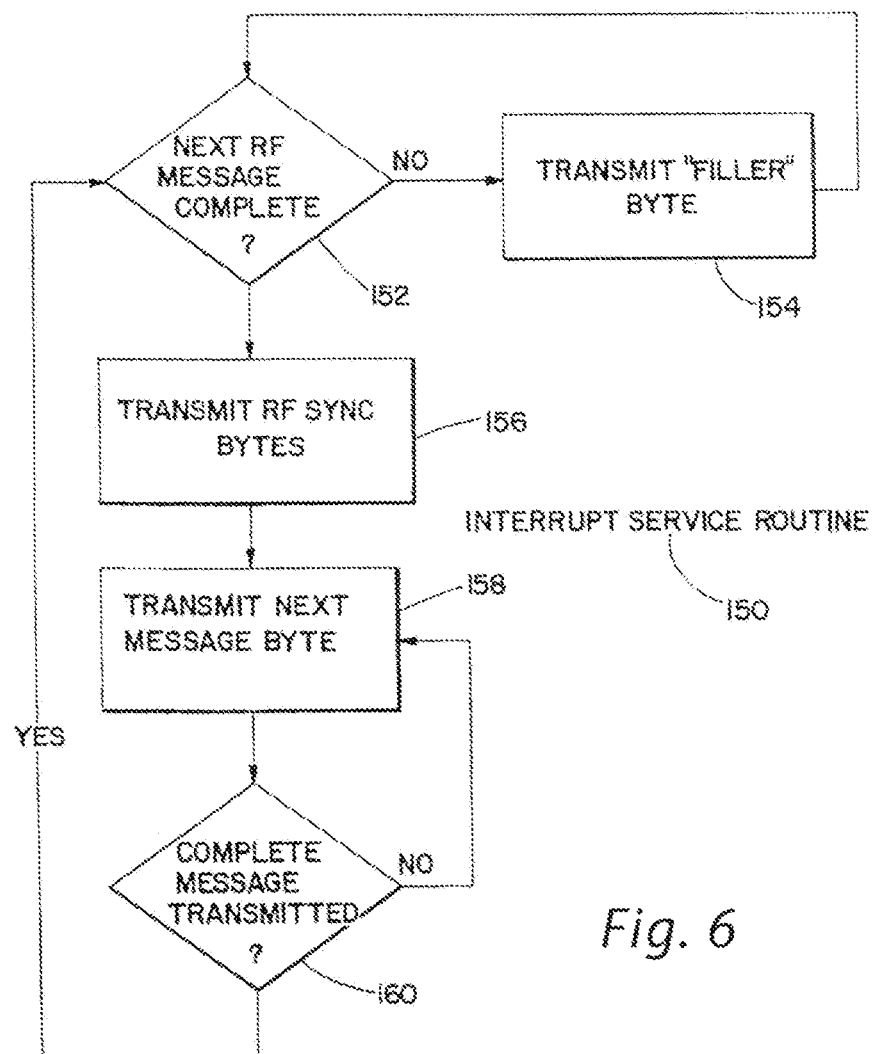
FIG. 6 is a block diagram of an embodiment of the programming of the interrupt service routine in the firmware in the signal processing module of part of the diagnostic device of the sleeping disorder treatment system of the present invention.

Referring now to FIG. 6 there is shown a block diagram of the software programming function of the ISR 150. The ISR is responsible for transmitting the individual message bytes over the RF carrier. The ISR is executed by a hardware interrupt which occurs immediately before every byte to be transmitted over the RF carrier. The ISR detects whether an RF message is completely filled 152. If the ISR detects (based on the flag variable) that an RF message is not yet completely filled by the main code, the ISR transmits a "filler" byte, or a byte with an even number of "1" and "0" bits 154. This acts to maintain an even (50%) modulation duty cycle on the carrier frequency.

Once the ISR detects that the main code has filled an RF message to be transmitted, it transmits the RF sync bytes 156. These are two unique bytes transmitted at the beginning of every RF message which are easily identified by the base station 40 as the start of a message.

Once the RF sync bytes have been transmitted, the ISR transmits each message byte of the RF message, in sequence 158. Once the RF message has been completely transmitted 160, the ISR resumes transmitting filler bytes until the next RF message is filled by the main code.

Because of the phase locked loop based frequency synthesizer used in the present invention, the module transmitter 28 and base transmitter 84 are frequency agile over the frequency range. Since the module receiver 29 and the base receiver 80 employ automatic frequency control, the present invention consumes relatively low power as the module transmitter 28 and base transmitter 84 can be intermittently powered down without loosing reception due to drift or sacrificing data transmission accuracy. The utilization of programmable firmware allows inexpensive and flexible operation for the inputting, conditioning and processing of any type, character and range of the external inputs. This also allows the module microcontroller 26, in response to the variation of the external inputs 12 or, in response to instructions received by RF signal through the module receiver 29, to adapt the signal processing module 16 based upon the variations allowing the signal processing means 16 to input, condition, process and transmit said external input notwithstanding said variation. The present invention performs this adaptation without the need to modify or alter hardware or select or use different hardware already present in the device. In other words all adaptation can be accomplished by software programming totally.

One or more sensors are used to develop the data or signals used in the present invention for determining a quantitative level of severity of a subject's sleeping disorder and/or symptoms. In various embodiments, preferably at least two EEG electrodes are used to develop this data. In other embodiments, preferably, at least two ECG electrodes are used. In still other embodiments, preferably a pulse oximeter is used. In still even other embodiments, preferably, either an $O^2$ or $CO^2$ blood gas monitor is used.

The signals from the one or more sensors used in various embodiments of the present invention are preferably analyzed using a processor and software that can quantitatively estimate or determine the severity of the subject's sleeping disorder or symptoms. Using either the microcontroller 26 of a data acquisition system, a separate computer, base station or processor, a PDA, a processor on a device for treating the subject's sleeping disorder or a combination of these processors, the severity of the subject's sleeping disorder and/or symptoms is determined and is used at least in part to regulate the physical or chemical treatment of the subject. Also optionally, the one or more sensors used in the system of the present invention can also be tethered to a computer, base station, cell phone, a PDA or some other form of processor or microprocessor.

The processor or microprocessor of various embodiments of the present invention can be part of a remote communication station or base station. The remote communication station or base station can also be used only to relay a pre- or post-processed signal. Preferably, the remote communication station or base station can be any device known to receive RF transmissions such as those transmitted by the wireless data acquisition system described herein. The remote communication station or base station by way of example but not limitation can include a communications device for relaying the transmission, a communications device for re-processing the transmission, a communications device for re-processing the transmission then relaying it to another remote communication station, a computer with wireless capabilities, a PDA with wireless capabilities, a processor, a processor with display capabilities, and combinations of these devices. Optionally, the remote communication station can further transmit data both to another device including the subject's treatment device and/or back. Further optionally, two different remote communication stations can be used, one for receiving transmitted data and another for sending data. For example, with the sleep diagnosis and treatment system of the present invention, the remote communication system of the present invention can be a wireless router, which establishes a broadband internet connection and transmits the physiological signal to a remote internet site for analysis, preferably for further input by the subject's physician or another clinician. Another example is where the remote communication system is a PDA, computer or cell phone, which receives the physiological data transmission, optionally re-processes the information, and re-transmits the information via cell towers, land phone lines, satellite, radio frequencies or cable to a remote site for analysis. Another example is where the remote communication system is a computer or processor, which receives the data transmission and displays the data or records it on some recording medium, which can be displayed or transferred for analysis at a later time.

The quantitative method for estimating or determining the severity of the subject's sleeping disorder or symptoms is preferably accomplished by using signals or data from the one or more sensors described herein. More preferably, this quantitative method is accomplished in real-time, allowing the subject's symptoms to be treated as they occur. By real-time it is meant that the quantitative diagnosis step is accomplished predictively or within a short period of time after symptoms occur which allows for immediate treatment, thereby more effectively reducing the health affects of such disorder while at the same time also minimizing side effects of the treatment chosen. By real-time, preferably the diagnosis is accomplished within 24 hours of receiving the signals from the one or more sensors on the subject, more preferably within 8 hours, even more preferably within 4 hours, still even more preferably within 1 hour, still even more preferably within 20 minutes, still even more preferably within 5 minutes, still even more preferably within 1 minute, still even more preferably within 10 seconds, still even more preferably within 1 second, still even more preferably within 0.1 seconds and most preferably within 0.01 seconds.

Various algorithms known to those skilled in the art are used to filter out noise from the signal or data, and to then quantify the level of severity of the subject's sleeping disorder or symptoms. This filtered data is then is preferably analyzed using the techniques described in the following paragraph In addition to these sleeping disorder data or signal analysis techniques various controller schemes can be used.

Various sleeping disorders have symptoms that can be predicted based on various combinations of physiological signals or data. Various embodiments of the present invention include the approach to identifying these symptoms prior to onset by identifying various characteristic shifts in the power spectrum of the sensors being used to monitor these physiological conditions. This characteristic shift in these signals or data can be identified and used to trigger an actuator on the physical or chemical treatment device(s) to provide for delivery of a certain level of treatment. The various embodiments of the present invention include but are not limited to the following signal-processing techniques that are utilized to predict the onset of these symptoms. These are: (i) the standard deviation technique, (ii) a recursively fit ARMAX system identification model, (iii) the Short-Time Fourier Transform (SFFT) technique, and (iv) time-frequency signal analysis with a variety of different kernels. The present invention would also include other on-line signal processing algorithms known to those skilled in the art, such as wavelet analysis, which is similar to time-frequency analysis with a particular kernel function, to identify the shift in power spectrum associated with imminent flow separation that is discussed herein.

The standard deviation technique operates on the principle that there is an increase in pressure fluctuation as the flow begins to separate from the surface of an airfoil, due to either increasing angle of attack or unsteady flow. A sharp increase in the standard deviation of pressure data is observed immediately prior to stall. To trigger the deployment the flow effectors and initiate fluid flow control, a threshold standard deviation can be calculated for each pressure sensor and programmed into the control strategy.

The second embodiment of a method to identify the shift in measured power spectrum of the signal from the pressure transducer to identify stall utilizes a recursively identified system model, particularly an Auto-Regressive Moving Average (ARMA) model. Advantageously, the controller is the ORICA™ controller, an extended horizon, adaptive, predictive controller, produced by Orbital Research, Inc. and patented under U.S. Pat. No. 5,424,942, which is incorporated herein by reference. The ARMA recursive identification method attempts to fit specific models to the measured data or signals. Evaluation of this data reveals distinct, identifiable model order shifts based, which can be used to actuate the treatment device at various levels. Further analysis of the frequency spectrum of the physiological data related to various sleeping disorders reveals recognizable changes in this data or signals. This clear characterization alongside the model order shifts allows the ORICA identifier to classify discrete models based upon various physiological conditions of the subject, thus allowing precisely controlled treatments to be delivered to the subject or patient. A simple function minimization based upon the error associated with each model will enable adaptive model selection for the subject's physiological condition. As the subject's physiological conditions moves toward various critical conditions or symptoms, the model with the best fit to the data will shift into a higher order model. This model shift foretells the onset of the symptom. A second sub-method of identifying impending symptoms using the ARMA and other related models is to track the poles of the identified system model based on the subject over time. As the subject's physiological condition moves toward certain designated critical symptoms, the poles of the identified system model will move toward a condition of symptom onset, thereby indicating to the control system that certain critical symptoms are impending. Either of these two signal identification techniques based on fitting a mathematical model to the system can be utilized to predict the onset of the subject's symptoms. The ARMA model can be adapted to resemble other canonical model forms thereby demonstrating similarity to other system identification methods based on Kalman filtering and similar approaches.

A third embodiment of a method for quantifying the power spectrum measured by the one or more sensors is by using Short-Time Fourier Transforms (STFT). A Discrete Fourier transform (DFT), and its numerically efficient complement the Fast Fourier Transform (FFT), both provide frequency information of a digitized signal or data from the sensors. The DFT and FFT both assume that the signal that is being measured is stationary in time. However, in the case of the subject being tested and treated, the measured signal or data is not stationary in time, which means a typical DFT/FFT approach is inapplicable. However, for short time periods the signal may be considered to be stationary. Therefore, it is possible to estimate the mean power spectrum by segmenting the physiological data or signals into epochs lasting anywhere from 0.1-5 seconds each, and then applying a discrete-time Fourier transform (DFT) to the windowed data. The DFT is used to calculate the power spectrum of the signal for that epoch. Then the spectral mean and median density are calculated from the power spectrum of the signals from each epoch. Using this method it is possible to identify specific frequency content in the data. As the subject begins to experience the onset of various critical symptoms, the frequency spectrum of the measured and analyzed data will shift, which indicates to the control system that the symptom is beginning.

A fourth embodiment of a signal processing method which can provide indications to the control system that various symptoms are impending, to enable either actuation of the treatment device, is to analyze the sensor data using a time-frequency transform. A time-frequency transform enables both frequency resolution and estimation stability for highly non-stationary signals, which typifies some types of such as some of the data or signals related to various physiological conditions. This is accomplished by devising a joint function of both time and frequency, a distribution that describes the energy and density of a signal simultaneously in both time and frequency. The general form of the time-frequency transform is given by the following $$P(t, w) = \frac{1}{4\prod^2} \int \int \int e^{-j\theta t - j\tau w + j\theta u} \phi(\theta, t) \cdot s^*\left(u - \frac{1}{2}\tau\right) s\left(u + \frac{1}{2}\tau\right) du \, d\tau \, d\theta$$

This transform can be used to calculate instantaneous power spectra of a given signal. The actual transformation distribution is selected by changing the kernel, $\Phi(\theta,\tau)$. The function [e-1] is interesting since it is possible to identify any distribution invariant to time and frequency shifts by means of its kernel, and the properties of the kernel are strictly related to the properties of the distribution, given by [e-1].

The diagnostic device of the present invention is used to provide an output which is then used either automatically to adjust the treatment device or by a clinician or the subject to adjust the device which provides the physical or chemical treatment device which is another part of the system of the present invention. There are clearly many embodiments of the present invention, and we will attempt to describe a few herein.

Various embodiments of the present invention include a device for physically or chemically treating a subject's sleeping disorder, which can be adjusted using the output of the level of severity of the subject's sleeping disorder. Physical and chemical methods to treat sleeping disorders are known to those skilled in the art. With the sleep disorder treatment system of the present invention those as well as new physical and chemical treatments can be used and developed for treating a subject's sleeping disorder because the system of the present invention allows for direct treatment of the disease and particularly of symptoms as they occur. Physical methods to therapeutically treat sleeping disorders and symptoms of these disorders include continuous positive airway pressure (CPAP), electrical stimulation of the muscles and nerves, and the like. Chemical methods to therapeutically treat sleeping disorders and symptoms while less common include various pharmaceutical agents with various delivery techniques including oral delivery, injection, transdermal delivery, injection with a controlled pump, inhalation therapy and the like.

The present invention is envisioned to be particularly valuable in the treatment of sleep apneas. With the present invention it is envisioned that modifications can be made to a subject's treatment regiment as the severity or level or the subject's symptoms increase or decrease better regulating the therapeutic treatment of the subject's sleeping disorder. For example, with a subject who has sleep apnea, delivery of a physical treatment such as CPAP can be adjusted during the treatment based on the sleep diagnosis results. The CPAP machine would preferably be set up to receive some type of signal, which would cause an adjustment in the flow rate or pressure of the breathing gas being delivered to the subject.

Figure 7:
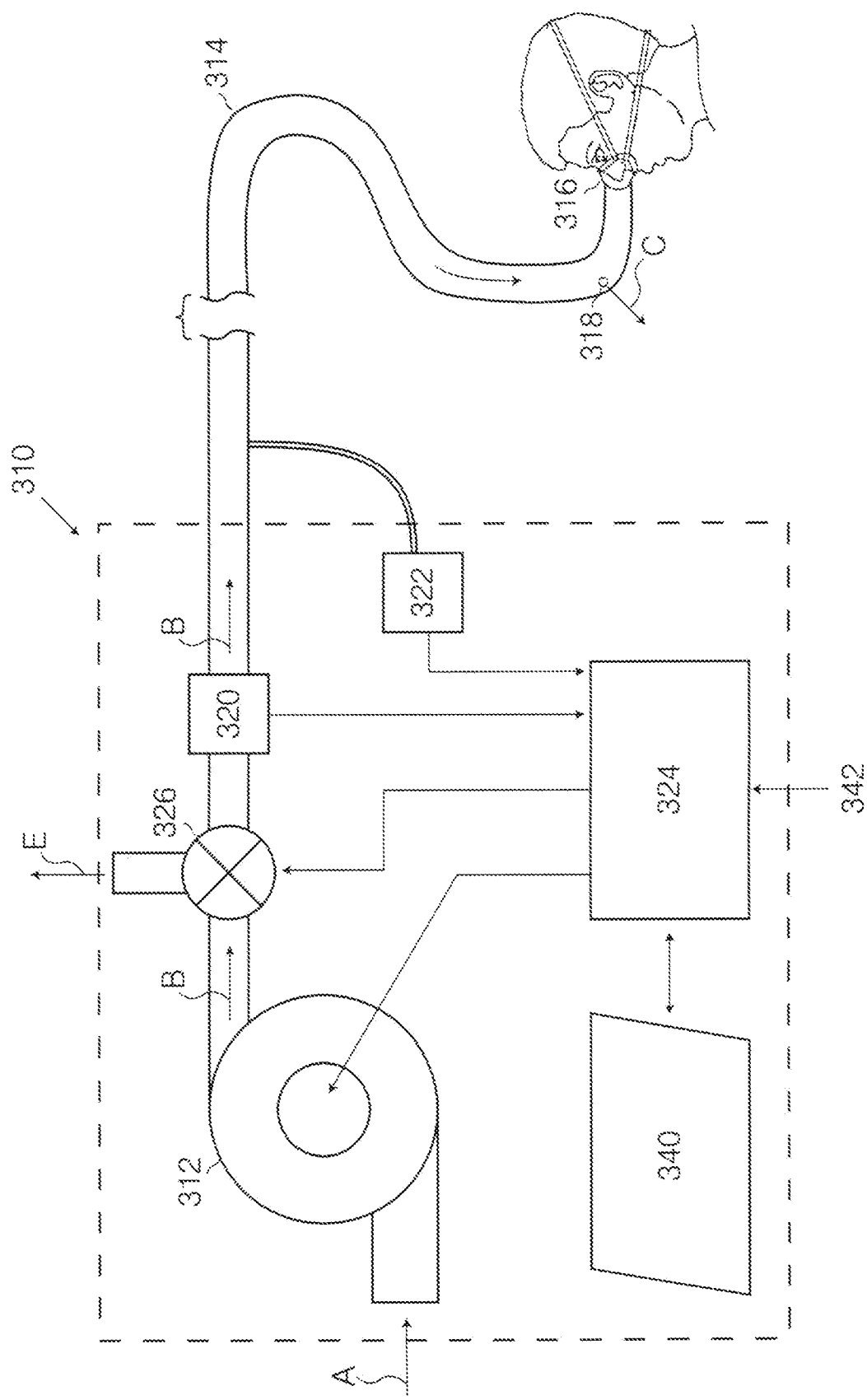
FIG. 7 is a schematic view of a pressure support system.

FIG. 7 shows a schematic view of one embodiment of a device that can be used to physically treat a subject's sleep disorder, which can be further adjusted using the output of the level of severity of the subject's sleeping disorder. More particularly, FIG. 7 shows a particular type of physical treatment device known as continuous positive airway pressure (CPAP) device. This conventional pressure support system 310 shown in FIG. 7 includes a pressure generator 312, a blower, piston or bellows, that receives a supply of gas from a gas source, such as ambient atmosphere, as indicated by arrow A, or pressurized gas tanks (not shown) and creates a flow of breathing gas, as indicated by arrows B, having a pressure greater than the ambient atmospheric pressure. A patient or subject circuit 314, which is typically a flexible conduit, delivers the elevated pressure breathing gas to the airway of the subject. Typically the subject circuit is a single limb conduit or lumen having one end coupled to the pressure generator and a patient interface device 316 coupled to the other end.

The subject interface device 316 connects the subject circuit 314 with the airway of the subject so that the elevated pressure gas flow is delivered to the subject's airway. Examples of subject interface devices include but are not limited to nasal masks, nasal and oral masks, full face masks, nasal canulas, oral mouthpieces, tracheal tubes, endotracheal tubes, hoods and the like. The single limb subject circuit shown in FIG. 7 also includes an exhalation port 318, also commonly referred to as an exhalation vent, exhaust port, or exhaust vent, to allow gas, such as expired gas from the subject, to exhaust to the atmosphere, as indicated by arrow C. Generally, the exhaust vent 318 is located in the subject circuit 314 near the subject interface device 316 or in the subject interface device itself.

A more sophisticated pressure support device of the present invention includes a flow sensor 320, pressure sensor 322, or both that monitor the flow and/or pressure of gas passing in the subject circuit 314. The flow information can also be used to determine the volume of gas passing through the subject circuit 314. The information from the flow sensor 320 and/or pressure sensor 322 is used, for example, to control the pressure or flow of gas provided to the subject, monitor the condition of the subject, monitor the usage of the pressure support device, any combination thereof, or the like.

Figure 8:
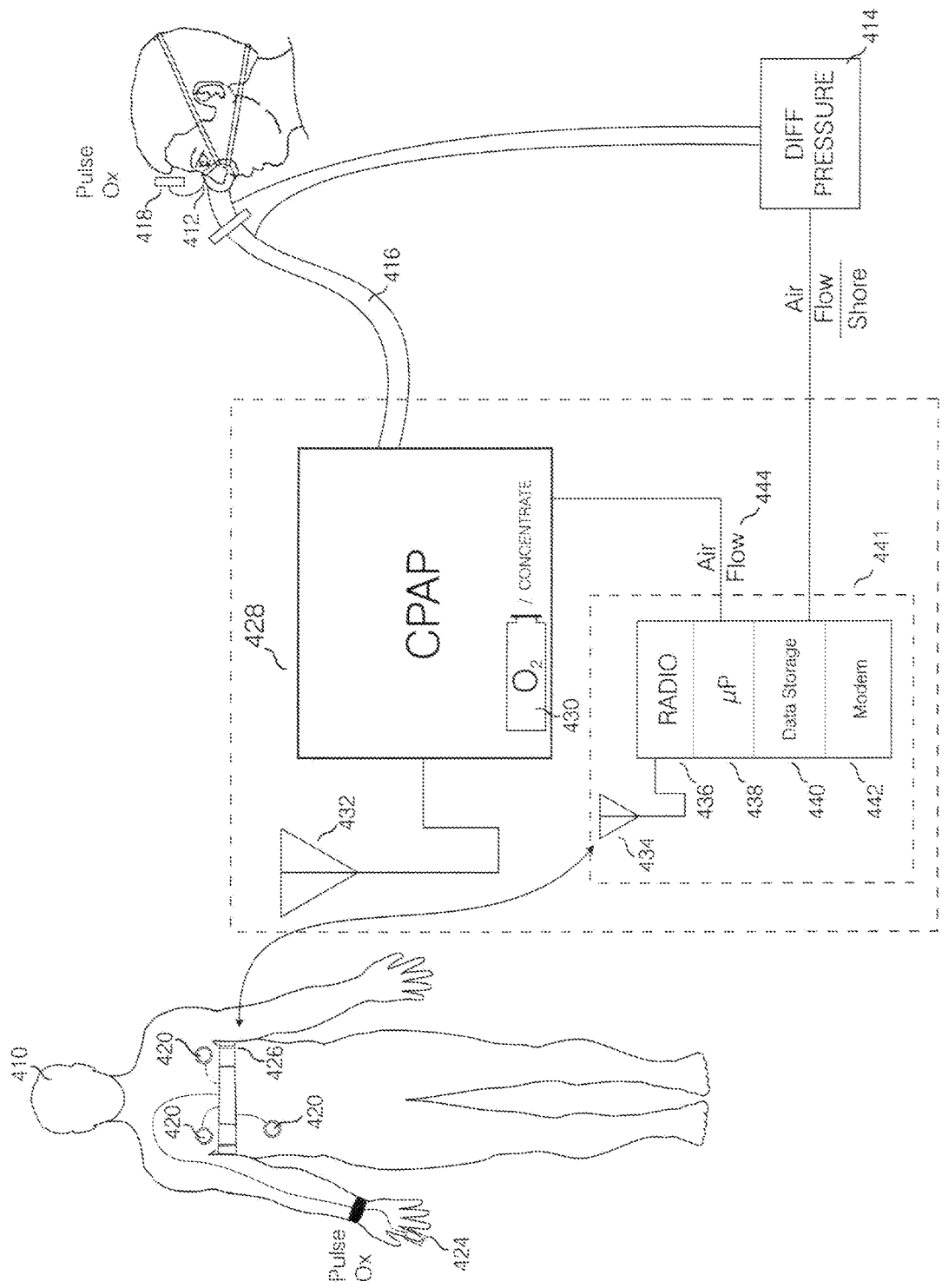
FIG. 8 is a schematic view of one embodiment of the sleep disorder treatment system of the present invention.

FIG. 8 shows a schematic view of one embodiment of the sleep disorder treatment system of the present invention. In FIG. 8, a subject 410 is hooked up with a number of sensors 420, 424, 418, and 426. The subject 410 in this case is shown with a respiratory mask 412, which is connected by an air hose or subject circuit 416 to a continuous positive air pressure device 428 similar to that shown in FIG. 7. The signal or data from one or more of these sensors is picked up in this embodiment by a diagnostic device 441, which comprises a radio 436 and antenna 434; a microprocessor 438 for processing the data or signals to determine a level of severity of the subject's sleeping disorder or symptoms; the diagnostic device then transmits a signal based on this level of severity by either a tether 444 or radio signal (not shown) to an actuator (not shown) in the CPAP device 428, which controls the flow of air or gas to the subject. The CPAP device 428 optionally has an $O^2$ tank connected, which can be used to increase the concentration of $O^2$ in the air being delivered to the subject. In addition, optionally the treatment device 428 has a sensor in the air hose 416, which can measure the differential pressure 414 and thereby accurately measure air flow provided to the patient. Also optionally, the device can have a nebulizer (not shown) with a reservoir and pump to injecting medication into the nebulizer.

It will be apparent to those skilled in the art that various modifications and variations can be made to the present invention without departing from the spirit and scope of the invention. Thus, it is intended that the present invention cover the modifications and variations of this invention provided they come within the scope of the appended claims and their equivalents.

The invention claimed is:

1. A positive airway pressure (PAP) sleep disorder treatment system comprising:
   a non-transitory computer readable medium comprising a first software, the first software adapted to be downloaded to a cell phone and executable by a first processor on the cell phone to display to a subject for viewing on the cell phone an index of treatment efficacy of the subject using a PAP device, the index based in whole or in part on a data of severity of sleep disorder symptoms of the subject and/or a data of usage of the PAP device by the subject, the cell phone comprising at least one first radio frequency wireless transceiver, the first processor, the first software when downloaded, and a display;
   the PAP device with an enclosure further comprising:
      a blower having an air output within the enclosure,
      an airflow sensor being any type of sensor internal to the enclosure of the PAP device adapted for measuring or deriving the respiratory airflow of a subject while using the PAP device and outputting airflow sensor data,
      a second processor within the enclosure adapted for receiving the airflow sensor data and for calculating:
         i) the data of a severity of the sleep disorder symptoms of the subject,
         ii) the data of usage of the PAP device by the subject, and/or
         iii) the index based in whole or in part on either i) or ii) or both i) and ii), a mask or a nasal cannula connected to the enclosure, and
      at least one second radio frequency wireless transceiver within the enclosure, the at least one second radio frequency wireless transceiver adapted for transmitting i) and ii), and/or iii); and
   a remote internet site, the remote internet site adapted for receiving i) and ii), or i), ii), and iii), related to the subject's treatment and the treatment's efficacy in whole or part, generated by the PAP device and transmitted via the at least one second radio frequency wireless transceiver.

2. The system of claim 1, wherein the remote internet site is adapted to be hosted on a remote communication system with a third processor and a recording medium for reprocessing, storing and/or outputting data received from the first and/or second radio frequency wireless transceiver in whole or in part, and to further output the reprocessed and/or the outputted data.

3. The system of claim 2, wherein the at least one second radio frequency wireless transceiver of the PAP device and the first radio frequency wireless transceiver of the cell phone are adapted to communicate using Bluetooth wireless protocol.

4. The system of claim 2, wherein the at least one second radio frequency wireless transceiver is adapted to transmit the data to the remote internet site in whole or in part via cell towers.

5. The system of claim 4, wherein the at least one second radio frequency wireless transceiver of the PAP device and the first radio frequency wireless transceiver of the cell phone are adapted to communicate using Bluetooth wireless protocol.

6. The system of claim 5, the PAP device further comprising at least one second software stored on a memory and executed by the second processor, the at least one second software which is adapted for calculating the data in whole or in part, wherein the PAP device is further adapted to be reprogrammed or to modify the at least one second software from the remote internet site or a second remote internet site.

7. The system of claim 4, the PAP device further comprising at least one second software stored on a memory and executed by the second processor, the at least one second software which is adapted for calculating the data in whole or in part, wherein the PAP device is further adapted to be reprogrammed or to modify the at least one second software from the remote internet site or a second remote internet site.

8. The system of claim 4, wherein the airflow sensor data is processed by the second processor, at least in part using one or more of the signal processing techniques from the group consisting of a standard deviation technique, a recursively fit ARMAX system identification model, a short-time Fourier transform technique, a discrete Fourier transform technique, a fast Fourier transform technique, a time-frequency signal analysis with a variety of different kernals, and a wavelet analysis.

9. The system of claim 4, wherein the remote internet site is adapted to retransmit to the first radio frequency wireless transceiver on the cell phone the data, in whole or in part, the data of i) and ii), or i), ii), and iii) or a second index related to the data of the subject's treatment and the treatment's efficacy calculated and transmitted by the PAP device.

10. The system of claim 9, wherein the remote communication system is further adapted to output a report and/or the reprocessed and/or outputted data to a printer and/or a second display for review by a clinician to determine the treatment efficacy.

11. The system of claim 2, wherein the airflow sensor data is processed by the second processor, at least in part using one or more of the signal processing techniques from the group consisting of a standard deviation technique, a recursively fit ARMAX system identification model, a short-time Fourier transform technique, a discrete Fourier transform technique, a fast Fourier transform technique, a time-frequency signal analysis with a variety of different kernals, and a wavelet analysis.

12. The system in claim 11, wherein the second processor of the PAP is configured to distinguish between and calculate the severity of both obstructive apneas and central apneas of the subject during a treatment with the PAP device.

13. The system of claim 2, wherein the remote internet site is adapted to retransmit the data to the first radio frequency wireless transceiver on the cell phone, in whole or in part, of i) and ii), or i), ii), and iii) related to the data of the subject's treatment and the treatment's efficacy calculated and transmitted by the PAP device.

14. The system of claim 2, wherein the PAP device further comprises an adaptive controller to adjust the flow of the blower based in part on the data of the severity of the symptoms of the subject calculated by the second processor.

15. The system of claim 14, wherein the PAP device further comprises an adaptive predictive controller to adjust the flow of the blower based in part on the data of the severity of the symptoms of the subject calculated by the second processor.

16. The system of claim 2, wherein the remote communication system is further adapted to output a report and/or the reprocessed and/or outputted data to a printer and/or a second display for review by a clinician to determine the treatment efficacy.

17. The system in claim 2, wherein the second processor of the PAP is configured to distinguish between and calculate the severity of both obstructive apneas and central apneas of the subject during a treatment with the PAP device.

18. The system of claim 1, wherein the PAP device further comprises at least one electronic component adapted to allow the PAP device to be adjusted remotely based on the data received by the remote internet site.

19. The system of claim 1, wherein the first software is adapted to be reprogrammed or modified remotely.

20. A positive airway pressure (PAP) sleep disorder treatment system comprising:
a non-transitory computer readable medium comprising a first software, the first software adapted to be downloaded to a cell phone and executable by a first processor on the cell phone to display to a subject for viewing on the cell phone an index of treatment efficacy of the subject using a PAP device, the index based in whole or in part on a data of severity of sleep disorder symptoms of the subject and/or a data of usage of the PAP device by the subject, the cell phone comprising at least one first radio frequency wireless transceiver, the first processor, the first software when downloaded, and a display;
the PAP device with an enclosure further comprising:
a blower having an air output,
an airflow sensor being any type of sensor internal to the enclosure of the PAP device adapted for measuring or deriving the respiratory airflow of a subject while using the PAP and outputting airflow sensor data,
a second processor adapted for receiving the airflow sensor data and for calculating:
i) the data of a severity of the sleep disorder symptoms of the subject,
ii) the data of usage of the PAP device, and/or
iii) the index based on either i) or ii) or both i) and ii),
a mask or a nasal cannula, and
at least one second radio frequency wireless transceiver, the at least one second radio frequency wireless transceiver adapted for transmitting i) and ii), and/or iii);
a second non-transitory computer readable medium comprising a second software adapted to be executable a third processor on a portable, wearable patient data acquisition device comprising a pulse oximeter and an accelerometer to collect additional physiological data from the subject for combining with the data collected by the PAP, the second software further adapted to forward the additional physiological data to combine with the data from the PAP device to determine the treatment efficacy of the subject using the PAP device; and
a remote internet site, the remote internet site adapted to receive i) and ii), or i), ii), and iii) related to the subject's treatment and the treatment's efficacy in whole or part, generated by the PAP device and transmitted via the at least one second radio frequency wireless transceiver and the additional physiological data collected with the portable, wearable patient acquisition device.

* * * * *